US011076790B2

(12) United States Patent
Kawabata et al.

(10) Patent No.: US 11,076,790 B2
(45) Date of Patent: Aug. 3, 2021

(54) BIOLOGICAL INFORMATION MEASURING APPARATUS

(71) Applicants: Shigenori Kawabata, Tokyo (JP);
Taishi Watanabe, Tokyo (JP)

(72) Inventors: Shigenori Kawabata, Tokyo (JP);
Taishi Watanabe, Tokyo (JP)

(73) Assignees: National University Corporation Tokyo Medical and Dental University, Tokyo (JP); Ricoh Company, Ltd., Tokyo (JP)

( * ) Notice: Subject to any disclaimer, the term of this patent is extended or adjusted under 35 U.S.C. 154(b) by 982 days.

(21) Appl. No.: 15/715,591

(22) Filed: Sep. 26, 2017

(65) Prior Publication Data
US 2018/0092561 A1    Apr. 5, 2018

(30) Foreign Application Priority Data

Sep. 30, 2016 (JP) .............................. JP2016-195107
Sep. 22, 2017 (JP) .............................. JP2017-182833

(51) Int. Cl.
| A61B 5/05 | (2021.01) |
| A61B 5/04 | (2006.01) |
| G01R 33/035 | (2006.01) |
| A61B 5/242 | (2021.01) |
| A61B 5/00 | (2006.01) |

(52) U.S. Cl.
CPC ............ *A61B 5/242* (2021.01); *A61B 5/0044* (2013.01); *A61B 5/407* (2013.01); *A61B 5/4029* (2013.01); *A61B 5/704* (2013.01); *A61B 2562/0223* (2013.01)

(58) Field of Classification Search
CPC ..... A61B 5/242; A61B 5/0044; A61B 5/4029; A61B 5/407; A61B 5/704; A61B 2562/0223
See application file for complete search history.

(56) References Cited

U.S. PATENT DOCUMENTS

| 6,628,978 B1 * | 9/2003 | Kondo .................. A61B 5/242 |
| | | 600/409 |
| 7,626,389 B2 | 12/2009 | Fiedler et al. |
| 8,583,208 B2 | 11/2013 | Adachi et al. |

FOREIGN PATENT DOCUMENTS

| JP | 2006-304851 | 11/2006 |
| JP | 2008-536600 | 9/2008 |
| JP | 2009-172175 | 8/2009 |
| JP | 2010-148578 | 7/2010 |
| JP | 4834076 | 12/2011 |
| JP | 5137149 | 2/2013 |
| WO | 2016/175020 | 11/2016 |

OTHER PUBLICATIONS

[0020] "Adachi et al.," "A SQUID system for measurement of spinal cord evoked filed of supine subjects," IEEE Transactions on Applied Superconductivity, col. 19 No. 3, Jun. 2009 pp. 861-866 (Year: 2009).*

* cited by examiner

*Primary Examiner* — Patricia J Park (74) *Attorney, Agent, or Firm* — IPUSA, PLLC (57) ABSTRACT

A biological information measuring apparatus includes a biomagnetism detector configured to detect biomagnetism of a subject, the biomagnetism detector including a temperature adjustment mechanism; and a radiation detector configured to acquire emitted radiation as digital image data. The radiation detector is disposed between a measurement region of the subject and the biomagnetism detector.

8 Claims, 5 Drawing Sheets

BIOLOGICAL INFORMATION MEASURING APPARATUS

CROSS-REFERENCE TO RELATED APPLICATION

The present application claims priority under 35 U.S.C. § 119 to Japanese Patent Application No. 2016-195107, filed on Sep. 30, 2016, and Japanese Patent Application No. 2017-182833, filed on Sep. 22, 2017, the contents of which are incorporated herein by reference in their entirety.

BACKGROUND OF THE INVENTION

1. Field of the Invention

The present invention relates to a biological information measuring apparatus.

2. Description of the Related Art

There are biological information measuring apparatuses for measuring weak biomagnetism generated from the heart, the spinal cord, and peripheral nerves, etc. of a subject. This biological information measuring apparatus has a function of detecting the magnetism generated by a weak current caused by excitation of cells constituting these organs. The technology of this biological information measuring apparatus is important for the diagnosis of heart diseases and nerve diseases, etc.

There are cases where morphological images are superimposed by an X-ray irradiation apparatus (for example, an X-ray irradiation apparatus using a film as described in Patent Document 1) at a different location from the biological information measuring apparatus.

Patent Document 1: Japanese Unexamined Patent Application Publication No. 2009-172175

SUMMARY OF THE INVENTION

An aspect of the present invention provides biological information measuring apparatus in which one or more of the disadvantages of the related art are reduced.

According to one aspect of the present invention, there is provided a biological information measuring apparatus including a biomagnetism detector configured to detect biomagnetism of a subject, the biomagnetism detector including a temperature adjustment mechanism; and a radiation detector configured to acquire emitted radiation as digital image data, wherein the radiation detector is disposed between a measurement region of the subject and the biomagnetism detector.

DETAILED DESCRIPTION OF THE PREFERRED EMBODIMENTS

In the related art, because the subject moves between the image diagnostic apparatus (an X-ray irradiation apparatus, etc.) and the biological information measuring apparatus, there has been a problem that the measurement results cannot be accurately matched. For example, when the subject moves between the X-ray irradiation apparatus and the biological information measuring apparatus, the body trunk (spine) of the subject may bend or warp in the anteroposterior direction or the lateral direction, or the joints of the extremity of the subject may bend or extend. Thus, it is extremely difficult to precisely match the position information of the subject obtained by the image diagnostic apparatus with the position of the subject at the time of an examination by the biological information measuring apparatus.

On the other hand, in order to detect image diagnosis results and biological information measurement results with high accuracy, a magnetic sensor with high sensitivity may be required.

A problem to be solved by an embodiment of the present invention is to provide a biological information measuring apparatus capable of detecting an image diagnosis result and a biological information measurement result with high accuracy and with ease.

Embodiments of the present invention will be described in detail; however, the present invention is not limited to the following embodiments, and may be appropriately modified within the scope of the object of the present invention.

The inventors of the present invention have found that X-rays can be detected in a state where a so-called X-ray detection digital panel apparatus, which is capable of acquiring emitted radiation as digital image data, is disposed between a magnetic sensor for measuring biomagnetism and the subject, and attained the present invention based on these findings. Specific examples will be described below.

<Biological Information Measuring Apparatus>

Figure 1:
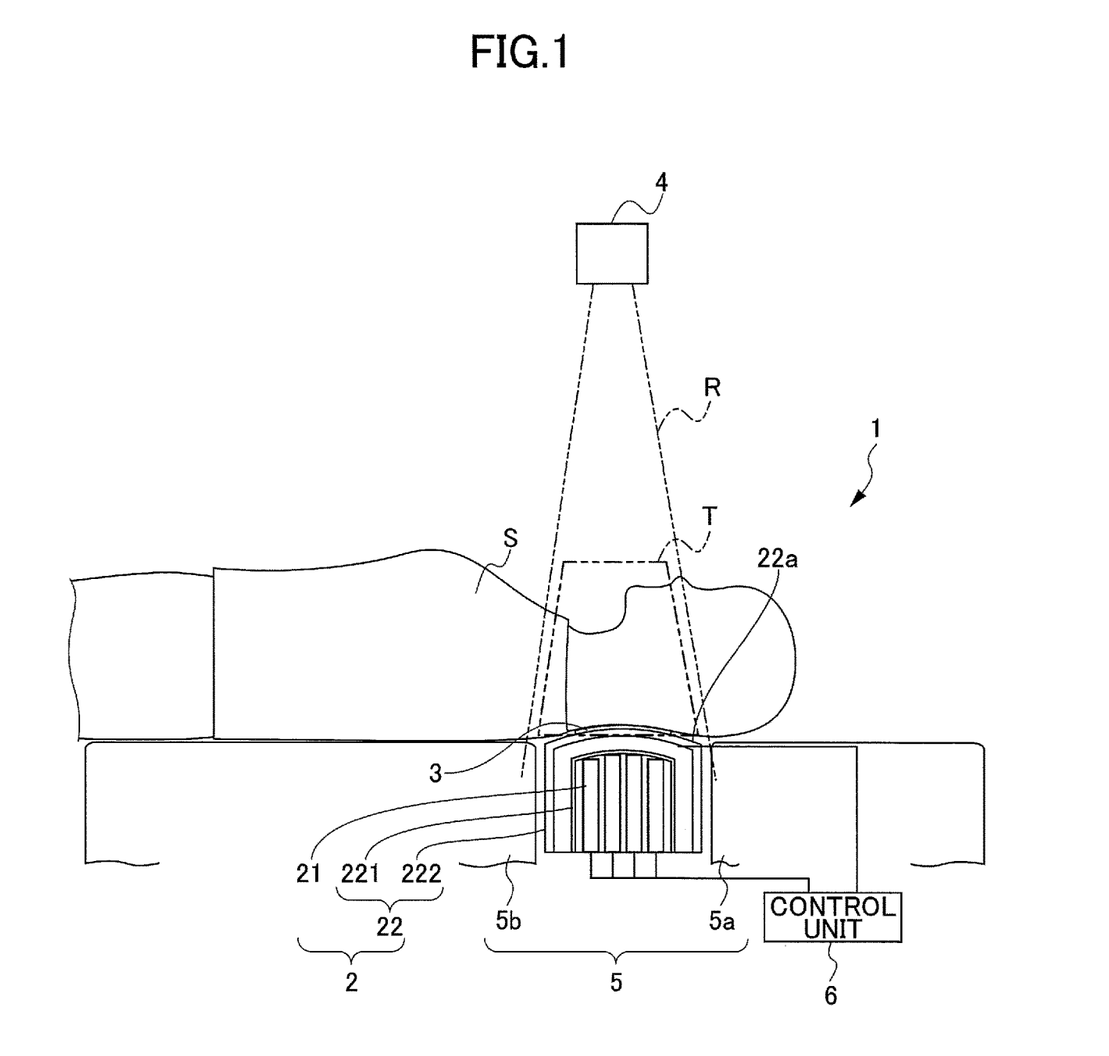
FIG. 1 is a diagram illustrating a configuration of a biological information measuring apparatus according to an embodiment of the present invention.

FIG. 1 is a diagram illustrating a configuration of a biological information measuring apparatus 1 according to the present embodiment. As illustrated in FIG. 1, the biological information measuring apparatus 1 includes a biomagnetism detecting unit 2 that includes a temperature adjustment mechanism and that is capable of detecting the biomagnetism of a subject, and a radiation detecting unit 3 capable of acquiring emitted radiation as digital image data. The radiation detecting unit 3 is disposed between a measurement region T of a subject S and the biomagnetism detecting unit 2. Furthermore, the biological information measuring apparatus 1 according to the present embodiment further includes a radiation emitting unit 4 that irradiates the subject S with radiation.

According to the biological information measuring apparatus 1 according to the present embodiment, the biomagnetism detection result obtained from the biomagnetism detecting unit 2, and a morphological image that is digital image data obtained from the radiation detecting unit 3, can be obtained by a single measurement operation, and the biomagnetism detection result and the morphological image can be accurately superimposed.

Hereinafter, the biomagnetism detecting unit 2, the radiation detecting unit 3, and the radiation emitting unit 4 will be described respectively.

[Biomagnetism Detecting Unit]

The biomagnetism detecting unit 2 includes a plurality of magnetic sensors 21 for detecting the biomagnetism, and an insulated container 22 for accommodating the plurality of magnetic sensors 21. The biomagnetism detecting unit 2 installed in a bed 5.

(Magnetic Sensor)

The magnetic sensor 21 detects the biomagnetism generated from the subject. Specific examples of the magnetic sensor 21 are a Superconducting QUantum Interference Device (SQUID) and an atomic magnetic sensor, etc. The SQUID sensor and the atomic magnetic sensor have detection sensitivities that are high enough to detect an extremely weak biomagnetism of approximately $10^{-18}$ T.

The plurality of magnetic sensors 21 are typically arranged in an array in the insulated container 22. By including the plurality of magnetic sensors 21, it is possible to obtain many pieces of biomagnetism information and to obtain more detailed biological information. The number and the arrangement method of the magnetic sensors 21 are not particularly limited, and the magnetic sensors 21 may be appropriately set according to the measurement region T of the subject S.

The detection signals detected by the magnetic sensors 21 are sent to a calculation unit (not illustrated). In the calculation unit, biomagnetism information is generated from the signals detected by the magnetic sensors 21, the biomagnetism information is converted into image information, and the image information is displayed on a display device.

(Temperature Adjustment Mechanism)

The temperature adjustment mechanism is a mechanism for adjusting the temperature of the magnetic sensors 21 to a predetermined temperature suitable for operations by the magnetic sensors 21. The temperature adjustment mechanism may be a known cooling device or heating device. For example, when the magnetic sensor 21 is a SQUID sensor, in order for the magnetic sensor 21 to attain a superconducting state, it is necessary to operate the magnetic sensor 21 at near absolute zero degrees. In the present embodiment, the insulated container 22 fulfills a part of the function of the temperature adjustment mechanism.

(Insulated Container)

For example, as illustrated in FIG. 1, the insulated container 22 includes an inner tank 221 and an outer tank 222. The plurality of magnetic sensors 21 are accommodated in the inner tank 221. The space between the inner tank 221 and the outer tank 222 is a vacuum space. A refrigerant such as liquid helium is supplied into the inner tank 221. Accordingly, in the biomagnetism detecting unit 2, the temperature is controlled to a temperature suitable for the magnetic sensors 21 to operate.

Although the shape of the insulated container 22 is not particularly limited, it is preferable that the surface facing the subject S (hereinafter referred to as a "distal end surface 22a") has a shape extending along the body surface of the measurement region T of the subject S. The shape of the distal end surface 22a may be flat or arcuate. For example, as illustrated in FIG. 1, when the biomagnetism detecting unit 2 is to function as a spinal magnetic meter, the shape of the distal end surface 22a is preferably arcuate.

Note that the insulated container is not limited to the insulated container 22 using a vacuum insulated container as illustrated in FIG. 1; the insulated container may be the insulated container 22 made of a foamed material, etc. The insulated container is preferably made of a non-magnetic material. When the insulated container 22 is made of a non-magnetic material, even when the insulated container 22 vibrates, it is possible to reduce the influence of the fluctuation of the environmental magnetism applied on the magnetic sensors 21. Examples of the non-magnetic material include a plastic material such as acrylic resin and nonferrous metals such as copper and brass.

(Bed)

The shape of the bed 5 is not particularly limited as long as the bed can hold the biomagnetism detecting unit 2. For example, as illustrated in FIG. 1, the bed 5 includes a head part bed 5a at which the head of the subject S is to be positioned, and a torso part bed 5b. The biomagnetism detecting unit 2 is disposed between the head part bed 5a and the torso part bed 5b, and is provided so as to face the measurement region T of the subject S.

Note that in FIG. 1, the biomagnetism detecting unit 2 is fixed to the bed 5; however, the biomagnetism detecting unit 2 may be configured to be movable with respect to the bed 5. When the biomagnetism detecting unit 2 is movable with respect to the bed 5, the biomagnetism detecting unit 2 may be moved to a desired measurement region T or may be brought into close contact with the body surface in the measurement region T.

Furthermore, although FIG. 1 illustrates a mode in which the subject S is measured on the bed 5 in a recumbent posture, the subject S may be measured in a sitting posture.

[Radiation Detection Unit]

The radiation detecting unit 3 is disposed between the measurement region T of the subject S and the biomagnetism detecting unit 2. The radiation detecting unit 3 acquires emitted radiation R as a morphological image that is digital image data.

The signals detected by the radiation detecting unit 3 are sent to a calculation unit (not illustrated). In the calculation unit, a morphological image is generated from the signals detected by the radiation detecting unit 3, the morphological image is converted to image information, and the image information displayed on a display device.

Incidentally, since the magnetism emitted by the subject S is weak, if the magnetized radiation detecting unit 3 is disposed between the biomagnetism detecting unit 2 and the subject S, the radiation detecting unit 3 will have a large influence on the result of detection by the biomagnetism detecting unit 2. Therefore, the radiation detecting unit 3 is made of constituent components that do not significantly affect the detection accuracy of the biomagnetism detecting unit 2.

For example, a flat panel detector (FPD) may be used as the radiation detecting unit 3.

As the FPD, there is a so-called direct conversion method in which charges are generated by a detection element in accordance with the dose of emitted radiation, and the charges are converted into electric signals. There is also a so-called indirect method in which emitted radiation is converted into electromagnetic waves of another wavelength such as visible light, by a scintillator, etc., and subsequently, charges are generated by a photoelectric conversion element such as a photodiode, etc., according to the energy of the converted and emitted electromagnetic waves, and the charges are converted into electric signals.

Generally, various components for performing these processes are incorporated in a casing such as a cassette, etc., in the FPD. However, as described above, since it is not preferable for the radiation detecting unit 3 to be magnetized, among the various components in the FPD used in the radiation detecting unit 3, various parts such as a circuit board, a control board, and a battery, etc., having a plurality of magnetic bodies, that can be disposed outside, are removed from the radiation detecting unit 3 and disposed outside. Furthermore, components that are conventionally made of metal, etc., such as the cassette, are formed of a non-magnetic material in the present embodiment, or such components are not used in the present embodiment.

In this way, it is preferable that the radiation detecting unit 3 does not greatly affect the detection accuracy of the biomagnetism detecting unit 2, by decomposing the components in the FPD, or by changing the materials of the components, etc. Furthermore, since it is preferable that the subject S and the biomagnetism detecting unit 2 are as close as possible to each other, it is preferable to remove the components, which can be disposed outside, from the radiation detecting unit 3, to reduce the thickness (in the direction orthogonal to the subject S) of the radiation detecting unit 3 as much as possible. For example, the thickness of the FPD is preferably approximately greater than or equal to 2 mm and less than or equal to 10 mm, and more preferably greater than or equal to 2 mm and less than or equal to 5 mm.

Furthermore, from the viewpoint of reducing the influence of the radiation detecting unit 3 applied on the detection accuracy of the biomagnetism detecting unit 2, the biological information measuring apparatus 1 preferably includes a control unit 6 capable of implementing control such that power is not supplied to the radiation detecting unit 3 while the biomagnetism detecting unit 2 is detecting the biomagnetism (while supplying power to the biomagnetism detecting unit 2). When power is supplied to the radiation detecting unit 3, electric charges are generated in the radiation detecting unit 3 and magnetism is generated, and this magnetism will be detected by the biomagnetism detecting unit 2.

Therefore, by controlling the power supply to the radiation detecting unit 3 by the control unit 6, it is possible to minimize the influence of the radiation detecting unit 3. Note that when obtaining detection results by the radiation detecting unit 3, power may or may not be supplied to the biomagnetism detecting unit 2; however, in terms of power saving, it is preferable not to supply power to the biomagnetism detecting unit 2 at this time.

Furthermore, it is preferable that the radiation detecting unit 3 is held in the biomagnetism detecting unit 2. That is, it is preferable that the relative positions of the biomagnetism detecting unit 2 and the radiation detecting unit 3 are fixed. By fixing the relative positions of the biomagnetism detecting unit 2 and the radiation detecting unit 3, the biomagnetism detection result obtained from the biomagnetism detecting unit 2 and the morphological image obtained from the radiation detecting unit 3 can be superimposed with high accuracy, without providing a position identifying means for identifying the position information of the biomagnetism detecting unit 2 and the radiation detecting unit 3.

The radiation detecting unit 3 may have any shape as long as the size corresponds to the desired measurement region T of the subject S. Preferably, the shape of the radiation detecting unit 3 extends along the distal end surface 22a of the biomagnetism detecting unit 2. When the distal end surface 22a has an arc shape, the radiation detecting unit 3 also preferably has an arc shape. Furthermore, the radiation detecting unit 3 may have flexibility so as to have a shape extending along the distal end surface 22a of the biomagnetism detecting unit 2.

Specifically, the installation position of the radiation detection unit 3 includes the following three modes (embodiments). Note that in order to configure the radiation detecting unit 3 so as to be fixed to the biomagnetism detecting unit 2 during measurement and to also be removable, a holding unit for holding the radiation detecting unit 3 at a desired position of the insulated container 22, may be provided. Examples of the holding unit are a rail, a groove, and a dent, etc. By providing such a guide (holding unit), even when the radiation detecting unit 3 is detached and attached during measurement, the radiation detecting unit 3 can be precisely positioned.

First Embodiment

Figure 2:
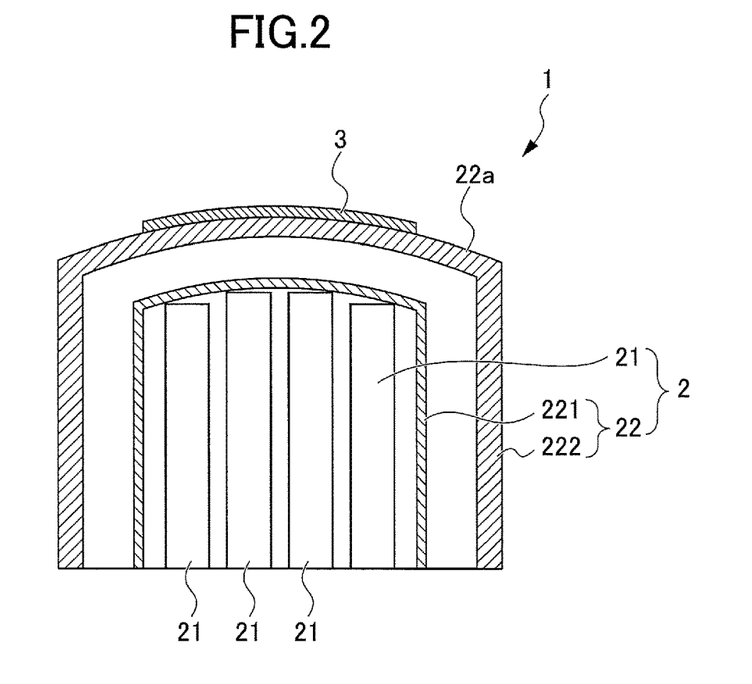
FIG. 2 is a cross-sectional view of a configuration of a main part of the biological information measuring apparatus according to a first embodiment of the present invention.

In the biological information measuring apparatus 1 according to a first embodiment, the radiation detecting unit 3 is provided outside the insulated container 22. FIG. 2 is a cross-sectional view of a configuration of a main part of the biological information measuring apparatus 1 according to the first embodiment. Note that in FIG. 2, the same members as those illustrated in FIG. 1 are denoted by the same reference numerals, and descriptions thereof are omitted.

As illustrated in FIG. 2, in the biological information measuring apparatus 1 according to the first embodiment, the radiation detecting unit 3 is disposed outside the insulated container 22, that is, disposed along the outer wall surface (the distal end surface 22a) of the outer tank 222. The radiation detecting unit 3 disposed on the outer peripheral surface of the distal end surface 22a of the insulated container 22 is easily detachable, and is thus easy to maintain. Furthermore, when only the detection result of the biomagnetism detecting unit 2 is necessary, the radiation detecting unit 3 may be removed from the biomagnetism detecting unit 2. Note that the radiation detecting unit 3 and the insulated container 22 may be integrated by an attachment.

Second Embodiment

Figure 3:
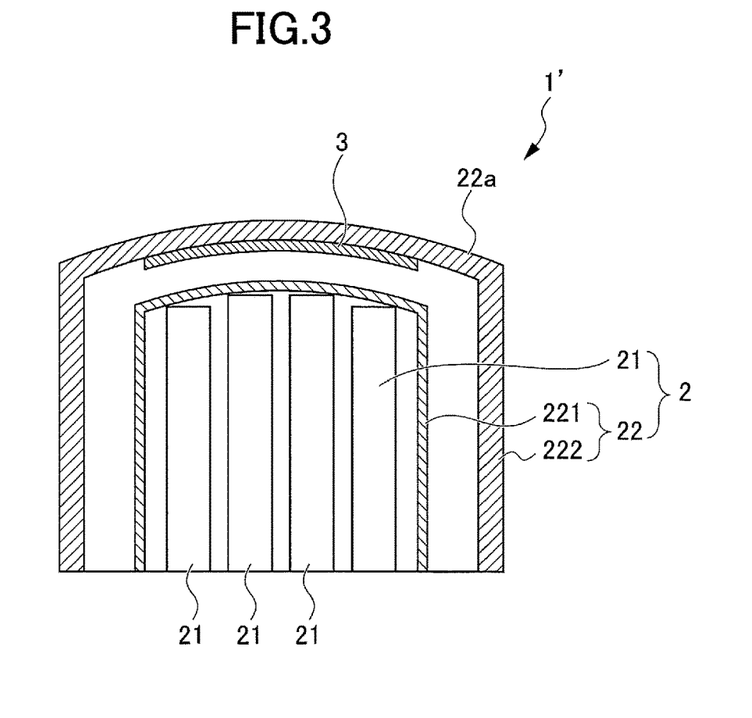
FIG. 3 is a cross-sectional view of a configuration of a main part of the biological information measuring apparatus according to a second embodiment of the present invention.

In a biological information measuring apparatus 1' according to a second embodiment, the radiation detecting unit 3 is provided inside the insulated container 22. FIG. 3 is a cross-sectional view of a configuration of a main part of the biological information measuring apparatus 1' according to the second embodiment. Note that in FIG. 3, the same members as those illustrated in FIG. 1 are denoted by the same reference numerals, and descriptions thereof are omitted.

As illustrated in FIG. 3, in the biological information measuring apparatus 1' according to the second embodiment, the radiation detecting unit 3 is disposed inside the insulated container 22, that is, disposed along the inner wall surface of the outer tank 222 opposed to the distal end surface 22a. Since the radiation detecting unit 3 is disposed on the inner wall surface of the outer tank 222 of the insulated container 22, the distance between the subject S and the magnetic sensors 21 becomes smaller than in the first embodiment, and the biomagnetism detecting unit 2 (the magnetic sensors 21) can increase the detection intensity of biomagnetism.

Third Embodiment

Figure 4:
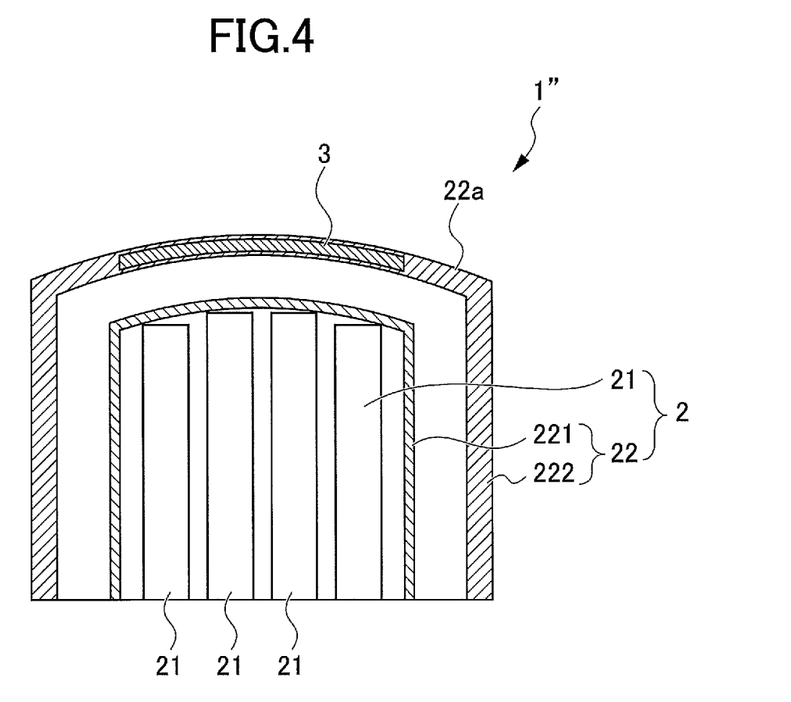
FIG. 4 is a cross-sectional view of a configuration of a main part of the biological information measuring apparatus according to a third embodiment of the present invention.

In a biological information measuring apparatus 1" according to a third embodiment, the radiation detecting unit 3 is provided inside a member of the insulated container 22. FIG. 4 is a cross-sectional view of a configuration of a main part of the biological information measuring apparatus 1″ according to the third embodiment. Note that in FIG. 4, the same members as those illustrated in FIG. 1 are denoted by the same reference numerals, and descriptions thereof are omitted.

As illustrated in FIG. 4, in the biological information measuring apparatus 1″ according to the third embodiment, the radiation detecting unit 3 is disposed inside a member of the insulated container 22, that is, inside the wall member of the outer tank 222 opposed to the distal end surface 22a. Since the radiation detecting unit 3 is disposed inside the wall member of the outer tank 222 of the insulated container 22, the distance between the subject S and the magnetic sensors 21 becomes smaller than in the first embodiment, and the biomagnetism detecting unit 2 (the magnetic sensors 21) can increase the detection intensity of biomagnetism.

[Radiation Emitting Unit]

As the radiation emitting unit 4, a known radiation emitting unit of the related art may be used, as long as the radiation emitting unit can irradiate a living body with radiation. In embodiments of the present invention, the term "radiation" is not limited to commonly used X-rays; radiation is a comprehensive concept including light beams produced by particles (including photons) discharged by radioactive decay, such as a rays, j rays, and y rays, etc., and light beams having energy greater than or equal to the aforementioned light beams, such as particle rays and cosmic rays, etc. Considering high versatility, it is preferable to use X-rays as the radiation.

[Measurement Procedure]

For example, as illustrated in FIG. 1, in an examination in which X-ray imaging and biomagnetism measurement of the spinal cord or the heart of a subject (human) are performed at the same time, the subject (human) S is placed in a supine position on the bed 5, and the subject (human) S waits at a predetermined position. The examiner operates an operation unit (not illustrated) to emit radiation from the radiation emitting unit 4 toward the subject S, and obtains an X-ray image that is the detection result from the radiation detecting unit 3. Subsequently, according to control by the control unit 6, power is supplied to the biomagnetism detecting unit 2 in a state where power is not supplied to the radiation detecting unit 3, and a spinal cord-induced magnetic field, etc., which is the detection result from the biomagnetism detecting unit 2, is obtained.

Alternatively, according to control by the control unit 6, the examiner may supply power to the biomagnetism detecting unit 2 in a state where power is not supplied to the radiation detecting unit 3, obtain a spinal cord-induced magnetic field that is the detection result from the biomagnetism detecting unit 2, and then emit radiation from the radiation emitting unit 4 toward the subject S, to obtain an X-ray image as a detection result from the radiation detecting unit 3.

Figure 5:
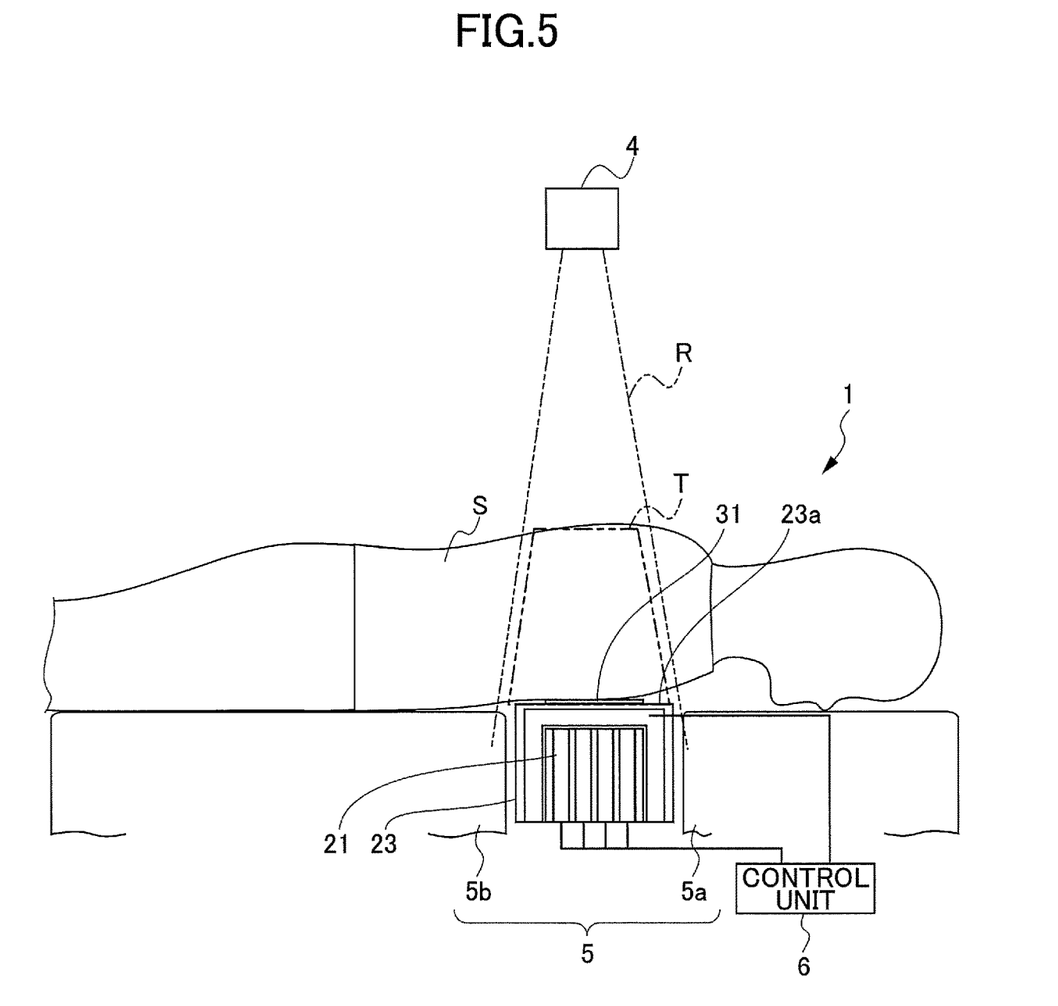
FIG. 5 is a configuration diagram of a biological information measuring apparatus according to another embodiment of the present invention.

Note that the biological information measuring apparatus according to the present embodiment is not limited to the mode illustrated in FIG. 1. FIG. 5 is a configuration diagram of a biological information measuring apparatus according to another embodiment. Note that in FIG. 5, the same members as those illustrated in FIG. 1 are denoted by the same reference numerals, and descriptions thereof are omitted.

For example, as illustrated in FIG. 5, in an examination in which X-ray imaging and biomagnetism measurement of the chest of a subject (human) are performed at the same time, the subject (human) S is placed in a prone position on the bed 5, and the subject (human) S waits at a predetermined position. Furthermore, when measuring the chest of the subject S, as illustrated in FIG. 5, as described above, the shape of a distal end surface 23a of an insulated container 23 is made flat and the shape of a radiation detecting unit 31 is also made flat such that the body surface of the subject S and the distal end surface 23a and/or the radiation detecting unit 31 are brought into close contact with each other.

The measurement region T of the biological information measuring apparatus according to the present embodiment is not limited to the spinal cord or the chest; the measurement region T may be other regions and organs such as the brain, etc. The distal end surface of the insulated container according to the present embodiment may have a suitable shape such that the distal end surface facing the subject S can be in close contact with the body surface in the measurement region T, in accordance with the measurement region T.

Note that it is preferable that the shape of the radiation detecting unit 3 also conforms to the shape of the distal end surface of the insulated container. For example, as described above, by forming the radiation detecting unit 3 with a flexible material, the radiation detecting unit 3 can be bent along the shape of the distal end surface of the insulated container. Furthermore, it is obvious that the magnetic sensors accommodated inside the housed inside the insulated container are to be disposed at optimum positions according to the shape of the insulated container.

Figure 6:
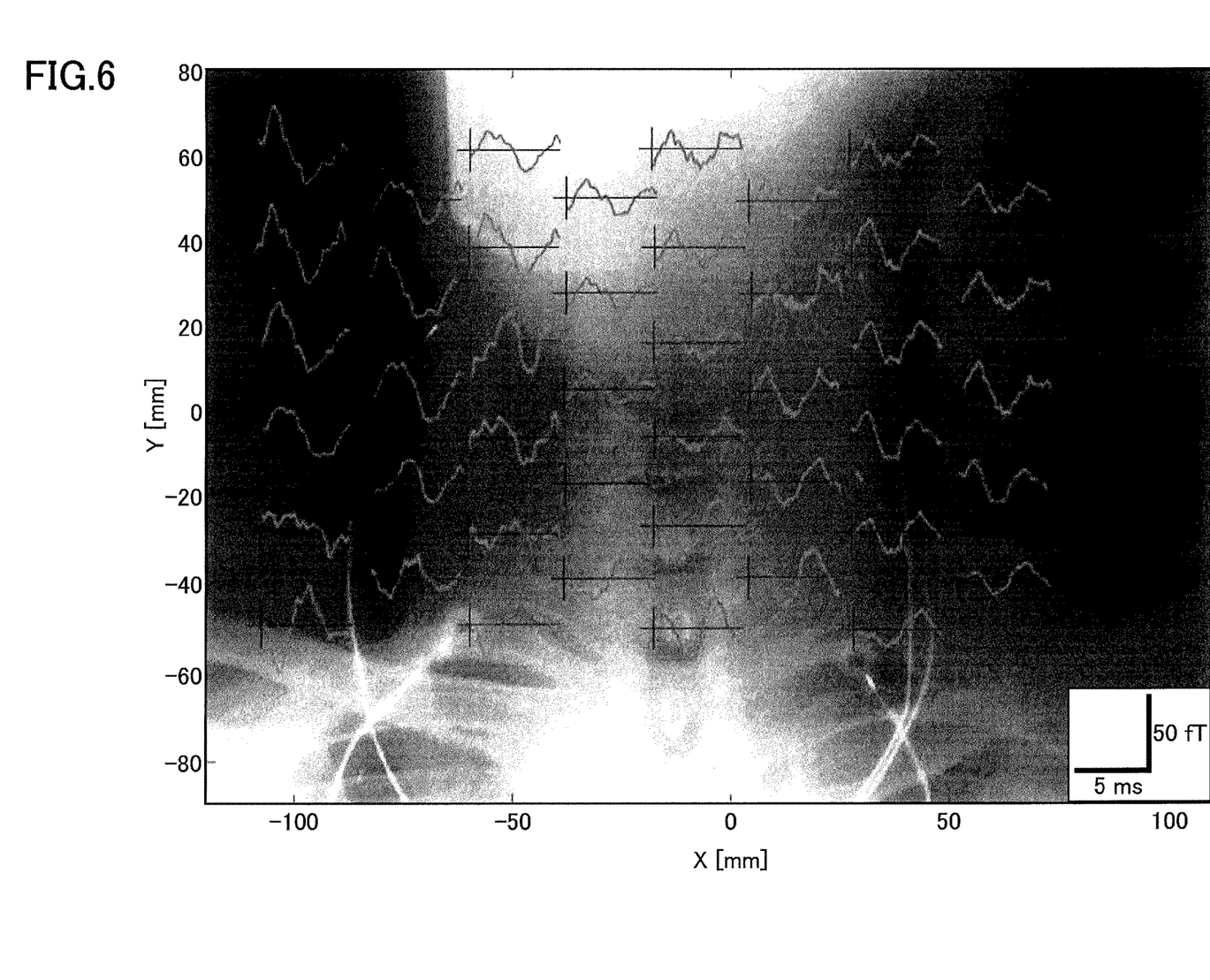
FIG. 6 is a diagram illustrating a measurement result in which a biological information measurement result and an X-ray image are superimposed.

The results of measuring the human spinal cord by the above-described biological information measuring apparatus 1 are illustrated in FIG. 6. As can be seen from FIG. 6, by a single measurement operation, it is possible to obtain biometric information, in which an X-ray image of the spinal cord and a spinal cord evoked field view are superimposed with each other with high accuracy.

According to one embodiment of the present invention, a biological information measuring apparatus capable of detecting an image diagnosis result and a biological information measurement result with high accuracy and with ease, can be provided.

The biological information measuring apparatus is not limited to the specific embodiments described in the detailed description, and variations and modifications may be made without departing from the spirit and scope of the present invention.

What is claimed is:

1. A biological information measuring apparatus comprising:
 a biomagnetism detector configured to detect biomagnetism of a subject, the biomagnetism detector including a temperature adjustment mechanism; and
 a flat panel detector configured to acquire emitted radiation as digital image data,
 wherein the flat panel detector is disposed between a measurement region of the subject and the biomagnetism detector,
 wherein the biomagnetism detector includes a plurality of magnetic sensors, and
 wherein the plurality of magnetic sensors are covered by an insulated container.

2. The biological information measuring apparatus according to claim 1, wherein the flat panel detector is disposed outside the insulated container.

3. The biological information measuring apparatus according to claim 1, wherein the flat panel detector is disposed inside the insulated container.

4. The biological information measuring apparatus according to claim 1, wherein the flat panel detector is disposed inside a member of the insulated container.

5. The biological information measuring apparatus according to claim 1, wherein a surface of the insulated container facing the subject, is arcuate or flat.

6. The biological information measuring apparatus according to claim 1, further comprising:
   a radiation emitter configured to irradiate the subject with the radiation.

7. The biological information measuring apparatus according to claim 1, further comprising:
   a controller configured to implement control such that power is not supplied to the flat panel detector while the biomagnetism detector is detecting the biomagnetism.

8. The biological information measuring apparatus according to claim 1, wherein the plurality of magnetic sensors includes a superconducting quantum interference device.

* * * * *